United States Patent [19]
Froehlich et al.

[11] Patent Number: 5,503,146
[45] Date of Patent: Apr. 2, 1996

[54] STANDBY CONTROL FOR CPAP APPARATUS

[75] Inventors: James P. Froehlich, Berlin; Joseph N. Mitchell, Rockwood; Stephen M. Jones, Turtle Creek, all of Pa.

[73] Assignee: DeVilbiss Health Care, Inc., Somerset, Pa.

[21] Appl. No.: 329,641

[22] Filed: Oct. 26, 1994

[51] Int. Cl.⁶ .................................................. A61M 16/00
[52] U.S. Cl. .............. 128/204.23; 128/202.22; 128/204.21; 128/205.25
[58] Field of Search .............. 128/204.18, 204.21, 128/204.23, 204.26, 205.13, 205.18, 205.24, 205.25, 202.22; 600/18

[56] References Cited

U.S. PATENT DOCUMENTS

| | | | |
|---|---|---|---|
| Re. 29,778 | 9/1978 | Stewart | 128/204.18 |
| 3,584,618 | 6/1971 | Reinhard et al. | 128/2.1 R |
| 4,239,039 | 12/1980 | Thompson | 128/205.24 |
| 4,522,194 | 6/1985 | Normann | 600/18 |
| 4,899,740 | 2/1990 | Napolitano | 128/202.22 |
| 4,924,862 | 5/1990 | Levinson | 128/207.16 |
| 4,944,310 | 7/1990 | Sullivan | 128/848 |
| 5,045,051 | 9/1991 | Milder et al. | 600/16 |
| 5,057,822 | 10/1991 | Hoffman | 340/611 |
| 5,065,756 | 11/1991 | Rapoport | 128/204.18 |
| 5,117,819 | 6/1992 | Servidio et al. | 128/204.18 |
| 5,134,995 | 8/1992 | Gruenke et al. | 128/204.23 |
| 5,148,802 | 9/1992 | Sanders et al. | 128/204.18 |
| 5,161,525 | 11/1992 | Kimm et al. | 128/204.26 |
| 5,199,424 | 4/1993 | Sullivan et al. | 128/204.18 |
| 5,203,343 | 4/1993 | Axe et al. | 128/725 |
| 5,239,995 | 8/1993 | Estes et al. | 128/204.23 |
| 5,245,995 | 9/1993 | Sullivan et al. | 128/204.23 |
| 5,259,373 | 11/1993 | Gruenke et al. | 128/204.23 |
| 5,313,937 | 5/1994 | Zdrojkowski | 128/202.22 |
| 5,335,654 | 8/1994 | Rapoport | 128/204.23 |
| 5,361,753 | 11/1994 | Pothmann et al. | 128/207.15 |

FOREIGN PATENT DOCUMENTS

| | | |
|---|---|---|
| 549299 | 6/1993 | European Pat. Off. |
| 2694697 | 2/1994 | France |
| WO93/25260 | 12/1993 | WIPO |
| 94/13349 | 6/1994 | WIPO |

OTHER PUBLICATIONS

Photocopy of brochure on the Puritan–Bennett Companion 319 Nasal CPAP System, dated May, 1993.
Photocopy of brochure entitled The Sullivan Nasal VPAP System, dated Jun., 1994.

*Primary Examiner*—Edgar S. Burr
*Assistant Examiner*—Eric P. Raciti
*Attorney, Agent, or Firm*—MacMillan, Sobanski Todd

[57] ABSTRACT

The invention relates to continuous positive airway pressure (CPAP) respiratory therapy apparatus for treatment of apnea, hypopnea and other sleep disorders, and particularly to a standby control for automatically operating an air blower in CPAP apparatus. A blower is connected through a hose and a mask, such as a nasal mask or a nasal cannula, to the patient's respiratory airway. Initially, the blower is in a standby mode in which it is either turned off or, preferably, operated at a low speed. When a patient starts breathing through the mask, the blower is automatically switched to an operating mode. In the operating mode, the blower may be controlled to initially supply a low air pressure to the mask which either is increased after a sufficient time delay to allow the patient to fall asleep or is increased in response to the detection of a respiratory event such as apnea or hypopnea. If patient breathing through the mask ceases because the mask has been removed or otherwise is no longer sufficiently sealed to the patient's airway, the blower is automatically returned to the low pressure standby mode. If the patient does not begin breathing through the mask within a predetermined time, the blower is stopped. An optional recorder measures the total time that the patient is breathing through the mask or the total time that the blower is in the operating mode to provide the prescribing physician or technician with patient compliance information.

19 Claims, 5 Drawing Sheets

STANDBY CONTROL FOR CPAP APPARATUS

TECHNICAL FIELD

The invention relates to respiratory therapy for treatment of sleep apnea, hypopnea, snoring and similar respiratory conditions and more particularly to a standby control for continuous positive airway pressure (CPAP) respiratory therapy apparatus.

BACKGROUND ART

Many sleep related respiratory conditions are caused by a blockage or a partial blockage of the respiratory tract. Snoring, for example, is caused by a partial blockage of the respiratory tract during inhalation. As the blockage increases, hypopnea or a reduction of air flow to the lungs occurs. Apnea, or a temporary cessation of breathing, can occur when the airway becomes totally blocked. A patient suffering from apnea may stop breathing for reoccurring intervals of from 10 seconds to two minutes or more for severe cases. The sleep apnea patient may have difficulty functioning in a normal manner during the day because of insufficient sleep caused by the apnea events. In severe cases, the patient also will suffer from problems caused by reduced blood oxygen levels.

One form of treatment for severe snoring, hypopnea and sleep apnea involves the application of a pneumatic splint to the patients respiratory tract while the patient sleeps. A sufficiently high continuous positive pressure is applied to the patient's airway to prevent its collapse or blockage. Typically, the applied positive pressure is within the range of from 3 to 20 cm $H_2O$. When the CPAP apparatus is initially turned on, the apparatus may immediately apply the prescribed pressure to the patient's airway. However, for improved patient comfort which in turn encourages patient compliance with the physicians prescribed treatment, it is desirable to maintain the applied pressure as low as possible while providing the desired therapeutic treatment. Various techniques have been used to minimize the applied pressure. For example, a more comfortable low pressure may be applied to the patient while the patient falls asleep. Generally, the patient will not suffer from hypopnea or apnea during this time. After sufficient time has elapsed for the patient to fall asleep, a controller gradually increases the applied pressure to the prescribed therapeutic level. Such a control is sometimes referred to as a "soft start". When the mask is first attached to the patient and the CPAP therapy apparatus is turned on, the pressure controller may be manually or automatically cycled to apply the full prescribed pressure to the patient for a short time to allow the patient to check and adjust for mask leaks.

In another known type of CPAP respiratory therapy apparatus, the pressure is automatically increased in increments from an initial low pressure in response to the sensing of snoring, hypopnea and/or apnea events. The pressure also may be gradually decreased over a period of time in the absence of such events. The CPAP therapy apparatus may delay any pressure increase for a time sufficient for the patient to fall asleep or may immediately look for abnormal breathing patterns. Systems of this type often sense snoring and other sounds occurring in the respiratory tract, or they may sense the absence of changes in the flow or pressure occurring between inhalation and exhalation during an apnea event, or they may sense the patient's breathing pattern through chest expansions and contractions.

The continuous positive pressure typically is applied to the patient through a nasal mask which is secured to the patient by suitable straps or headgear. When the system has a soft start capability, the patient will attach the mask and press a "start" switch. A blower will apply a low pressure to the patient for a preset time interval, such as 10, 20 or 30 minutes. In some systems, the patient can select the low pressure time interval. Either continuously over the set delay time or towards the end of the set time or after expiration of the set delay time, the pressure is gradually increased to the prescribed level. Or, after the mask is secured to the patient in an automated system, a start switch is pressed, and a low pressure is applied to the patient until a controller senses a respiratory condition which requires a higher pressure.

If the mask is accidentally knocked off or removed by the patient during sleep or if the mask is moved to a position creating a large leakage between the mask and the patient or if the patient begins open mouth breathing, an automatic pressure controller may assume that the patient has stopped breathing because of an apnea event and may automatically increase the pressure to the maximum prescribed level. If a patient undergoing CPAP therapy must get up and temporarily remove the mask during the night, it is necessary for the patient to remember to manually restart the CPAP controller alter the mask in reattached. If the apparatus is left on while the mask is temporarily removed, the controller will respond as if the patient has experienced an apnea event and will increase the mask pressure to the maximum level. The patient then will be subjected to the maximum pressure when the mask is reattached.

DISCLOSURE OF INVENTION

According to the invention, a standby control is provided for automatically starting and stopping operation of CPAP apparatus. The control operates in response to the sensed patient breathing pattern. Preferably, patient breathing is sensed by sensing air flow or air pressure changes occurring in the closed air system between a blower or compressor which creates the positive air pressure and a mask connected to the patient's airway. As used herein, the term "mask" and "nasal mask" are intended to include a nasal mask which seals over a patient's nose, a face mask which seals over the mouth and nose of a patient, a cannula which seals to the nares of a patient's nose, and any similar device which is capable of applying a positive airway pressure to the patient's respiratory system. The term "blower" shall mean any device capable of creating air flow at a positive pressure suitable for respiratory therapy.

Initially, the CPAP apparatus may be placed in a standby mode wherein the electronic controller is turned on and the blower remains off. Or, preferably, the apparatus is placed in a low pressure standby mode in which the compressor is operated at a constant low speed to create a low positive pressure air flow. The patient secures the mask in a conventional manner and begins breathing through the mask. The apparatus is designed to allow the patient to breath through the mask while the blower is off. Once the mask is secured to the patient and the patient begins breathing into the mask, the controller senses breathing pattern changes. After sensing a predetermined number of breaths, the controller turns the blower on if it was previously off and either begins a soft start cycle for a fixed cycle system or begins looking for breathing patterns which indicate a need for a higher pressure in an automatic pressure adjust system.

In the event that there is a gross air leak in the system, such as when the mask is removed from the patient, the controller senses the total absence of breathing patterns and/or the high air flow and/or low air pressure in the system. After a predetermined time with high air flow, the controller stops the air blower and the system enters the standby operating mode. The apparatus initially may enter a low pressure standby mode and, if no breathing is sensed during a predetermined time interval, may be switched to a blower off standby mode. When the patient reattaches the mask and begins breathing into the mask, the controller will again start controlling the blower and increase the applied pressure, for example, with a soft start cycle or with full pressure or with an automatic pressure adjust cycle. If desired, the CPAP apparatus may include a recorder or timer which measures the total time the apparatus is used each night by the patient. The apparatus use time can be accurately measured, since the system can be controlled to operate the timer only when the patient is breathing into the mask or only while the apparatus is in its normal operating mode. Prior art CPAP systems only measured the on time whether or not the patient was connected to the system and would not automatically interrupt the time measurement when the patient removed the mask.

Accordingly, it is an object of the invention to provide a standby control for automatically operating an air blower in CPAP apparatus.

Other objects and advantages of the invention will become apparent from the following detailed description of the invention and the accompanying drawings.

BEST MODE FOR CARRYING OUT THE INVENTION

Figure 1:
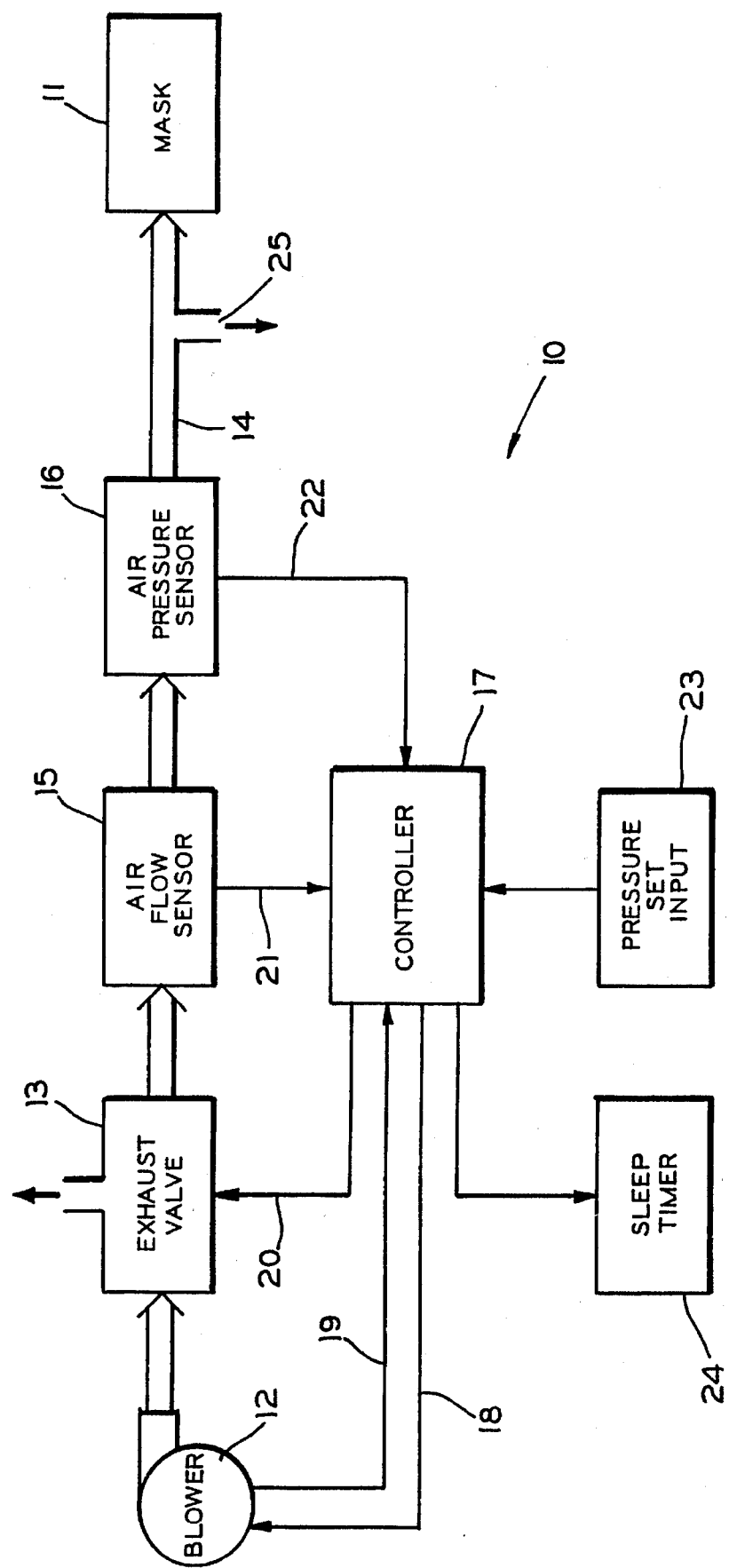
FIG. 1 is a block diagram of CPAP apparatus according to the invention.

Referring to FIG. 1 of the drawings, a block diagram is shown for CPAP apparatus 10 according to a preferred embodiment of the invention. The apparatus 10 has a mask 11 which is secured to a patient by suitable straps or headgear (not shown) in a conventional manner. The mask 11 may be, for example, a nasal mask which covers and is sealed to the patient's face around the nose, a face mask which covers and is sealed around both the nose and mouth or a nasal cannula which engages and seals to the patient's nares.

A centrifugal blower 12 or other suitable source of compressed air is connected through an optional exhaust valve 13 and a flexible, kink resistant pressurized air delivery tube 14 to the mask 11. A flow sensor 15 and a pressure sensor 16 are connected at any point downstream of the exhaust valve 13 to measure air flow and air pressure delivered through the mask 11 to a patient. The apparatus 10 is operated by a controller 17 which includes signal processing circuitry and a programmed digital microprocessor. The controller 17 is connected through a line 18 to drive the blower 12 and the blower is connected through a line 19 to provide a feedback speed signal to the controller 17. The controller 17 is connected through a line 20 to control the optional exhaust valve 13, as will be discussed below. The air flow sensor 15 provides an accurate air flow rate signal over a line 21 to the controller 17 and the air pressure sensor 16 provides an air pressure signal over a line 22 to the controller 17.

The air flow rate sensor 15 must be capable of providing an accurate flow rate signal which responds to air flow variations between inspiration and expiration and preferably is responsive to flow fluctuations caused by snoring. Preferably, the air flow sensor 15 consists of a laminar flow element (not shown) connected in series with the air delivery tube 14 and a mass flow transducer (not shown). The laminar flow element and the mass flow transducer are connected in parallel. Most of the air flow from the blower 12 to the tube 14 passes through the laminar flow element to create a pressure drop which is directly proportional to the air flow rate. A smaller portion of the air flow will pass through the mass flow transducer to produce a signal which is directly proportional to the pressure drop across the laminar flow element and hence a signal which is directly proportional to the total air flow delivered to the tube 14.

The prescribed maximum CPAP pressure, or the inspiration positive airway pressure (IPAP) is set by a suitable input device 23, such as pressure set switches, which are connected to or a part of the controller 17. Finally, the controller 17 may be connected to an optional sleep timer 24 which measures the total time that the patient is wearing the mask 11. It will be appreciated that the blower 12, the exhaust valve 13, the sensors 15 and 16, the controller 17, the pressure set input 23 and the sleep timer 24 may all be mounted in a single base unit cabinet (not shown) connected through the hose 14 to the mask 11. Since the air pressure in the mask 11 is a function of the pressure inside the base unit and the pressure loss in the delivery hose 14, which in turn is a function of the flow through the hose 14, the pressure signal and the flow signal may be combined to produce a signal that accurately represents the pressure at the mask 11. The signals may be combined in the controller either with analog circuitry or digitally by the programmed microprocessor.

The controller 17 may operate the blower 12 to provide one or more of several known operating modes. In one known type of CPAP apparatus, the blower 12 is immediately operated to provide the prescribed pressure through the mask 11 to the patient when the apparatus 10 is turned on. In another known type of CPAP apparatus, the blower 12 initially applies a low pressure to the patient for improved patient comfort while falling asleep. Patient compliance with the prescribed therapy is increased by promoting patient comfort. After a set time delay sufficient for the patient to fall asleep, the apparatus automatically ramps the pressure up to the prescribed pressure. This mode of operation is sometimes referred to as "soft start". Or, the apparatus may have an automatic operating mode which initially starts at a low pressure and automatically adjusts the applied pressure up and down, but no greater than a set maximum prescribed pressure. Adjustments may be based on sensing the presence and absence of hypopnea and/or apnea events and/or precursors to apnea such as snoring. Apparatus of this type tries to maintain the minimum pressure necessary to prevent the occurrence of hypopnea and apnea events.

According to the invention, the controller 17 also may provide a standby operating mode for the blower 12. When the apparatus 10 is initially turned on, the blower 12 may remain off or it may be operated at a low speed to provide a constant low air flow to the mask 11. When the controller 17 senses breathing in the mask 11, the controller 17 begins either a soft start cycle or an auto adjust cycle which is responsive to the detection of hypopneas, apneas and/or precursors to apnea such as snoring. If the blower 12 is initially operated at a low pressure standby mode for a predetermined time, such as 15 minutes, without sensing breathing, the controller 17 may turn the blower 12 off.

Normally, one or more calibrated vent openings 25 are provided either in the mask 11 or in the delivery tube 14 adjacent the mask 11. A portion of the air flow through the tube 14 and expiratory air from the patient are discharged through the vent opening 25. When the patient inhales, the air pressure as sensed by the sensor 16 will drop slightly and when the patient exhales, the air pressure sensed by the sensor 16 will tend to increase slightly. The positive airway pressure provides a pneumatic splint to keep the airway expanded during inhalation for free air flow to the lungs. The pneumatic splint is not needed during exhalation and the patient must exhale against any applied pressure, which can cause some patient discomfort. The optional exhaust valve 13 may be used to reduce the applied pressure during exhalation. When the controller 17 senses that expiration has began, the exhaust valve 13 is opened to vent a portion of the air flow from the blower 12 to atmosphere, thus reducing the expiratory positive airway pressure (EPAP) at the mask 11. Thus the CPAP apparatus 10 may be operated in a bilevel mode wherein different pressures are applied to the patient during inhalation and exhalation. It will be appreciated that although a specific embodiment has been described for generating signals for controlling the exhaust valve 13 for the bilevel operating mode, other circuit arrangements will be apparent to those skilled in the art. If the apparatus 10 is provided with a bilevel operating mode, both the desired EPAP pressure and the desired IPAP pressure may be set with the pressure set input 23.

Figure 2:
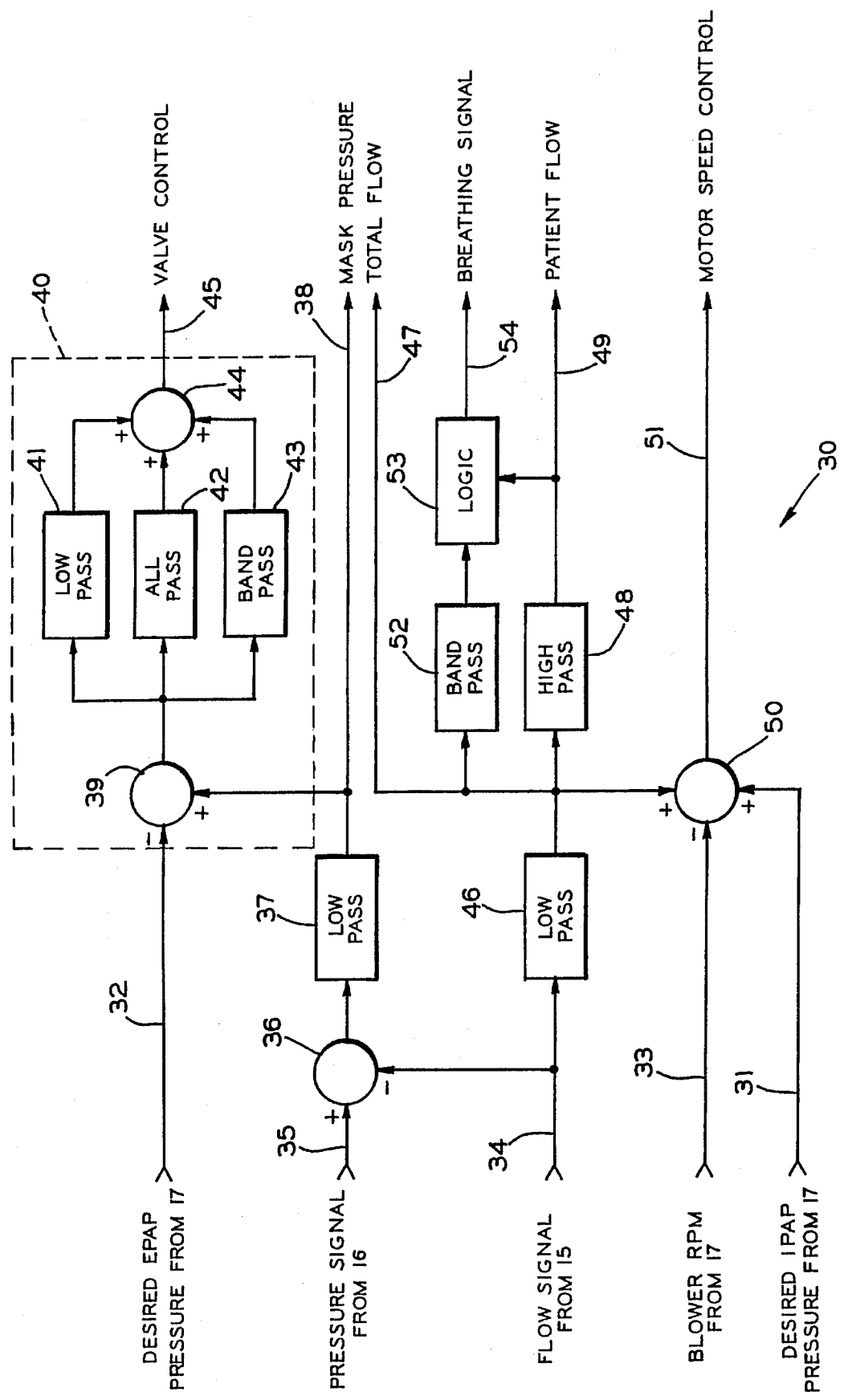
FIG. 2 is a schematic block diagram of signal filtering circuitry portion of the controller of FIG. 1.

FIG. 2 is a block diagram of a portion of the controller 17 illustrating circuitry 30 used in conjunction with a programmed microprocessor for controlling the blower 12 and the exhaust valve 13 and for providing information on the operation of the CPAP apparatus 10 according to one embodiment of the invention. The exemplary circuitry 30 has five analog inputs: an input 31 indicative of the desired IPAP pressure, an input 32 indicative of the desired EPAP pressure, an input 33 representing the actual blower speed from the line 18 (FIG. 1), an input 34 representing the air flow in the hose 14 from the sensor 15 (FIG. 1) and an input 35 representing the air pressure in the hose 14 from the sensor 16 (FIG. 1). The desired IPAP pressure input 31 and the desired EPAP input 32 are analog signals which may be established by the microprocessor and the pressure set inputs 23. If the apparatus 10 does not have a bilevel operating mode, then the EPAP input 32, the filter 40, the valve control output 45 and the exhaust valve 13 are omitted. The input 31 then becomes redefined as indicative of the desired CPAP pressure.

As indicated above, the pressure at the mask 11 is a function of the pressure signal and the flow signal as measured by the sensors 16 and 15, respectively. The pressure signal on the input 35 and the flow signal on the input 34 are combined at an amplifier 36 to produce a signal representing the mask pressure. This signal is passed through a low pass filter 37 which attenuates high frequency noise and produces a clean mask pressure signal on an output 38. The mask pressure signal on the output 38 and the desired EPAP pressure signal on the input 32 are applied to a filter 40 wherein they are combined at an amplifier 39 to create an error signal. In the filter 40, the error signal is applied in parallel to a low pass filter 41, an all pass filter 42, a band pass filter 43 and a summing amplifier 44 to produce a valve control signal on an output 45 for operating the exhaust valve 13 (FIG. 1). The valve control output 45 controls how much air is vented by the valve 13 during exhalation. The microprocessor determines when exhalation is taking place and the valve 13 should be opened and controls the input 32 accordingly.

The flow signal on the input 34 also is passed through a low pass filter 46 which attenuates high frequency noise and produces a clean total air flow signal on an output 47. The low pass filter 46 removes snoring noise from the flow signal. The low pass filter 46 may have, for example, a cutoff frequency of about 20 Hz. The total air flow signal from the filter 46 also is applied through a high pass filter 48 which eliminates the DC component of the signal which is caused by continuous leakage flow through the expiration vent opening 25 and through any leakage between the mask and the patient's face. The DC flow signal component also may be caused in part by open mouth breathing when the patient keeps his or her mouth open while breathing through the nose. A portion of the air flow to the patient's nose may be continuously vented through the open mouth. The resulting output from the filter 48 is a patent flow signal which is applied to an output 49. This signal accurately represents the air flow to the patient's lungs during inspiration and from the patient's lungs during expiration.

The desired IPAP pressure motor control voltage is calculated at a summing amplifier 50 in response to the total flow signal from the low pass filter 46, the blower speed input 33 and the desired IPAP input 31 from the microprocessor to produce a motor speed control output 51 for establishing the desired inspiratory pressure at 100 LPM (liters per minute) total flow produced by the blower 12. The blower motor control voltage is constant for the desired IPAP. Below a pressure set point of 10 cm $H_2O$, the blower motor speed is maintained at the 10 cm $H_2O$ set point.

For producing a breathing signal square wave, the total flow signal from the low pass filter 46 also is passed through a band pass filter 52 which produces the mathematical derivative of the flow signal. The band pass filter 52 is of a type known as a "practical differentiator". The reason for using the total flow derivative is that in certain circumstances the derivative of the total flow signal responds more quickly to inspiratory and expiratory efforts than the patient flow signal. The flow derivative signal is passed with the patient air flow signal from the high pass filter 48 to logic 53 which produces a square wave breathing signal output 54. This signal is used, for example, by the microprocessor for determining when to change operating modes and for controlling the opening and closing of the optional exhaust valve 13 (FIG. 1).

Ideally, the patient air flow signal would be a smooth noiseless signal and the zero reference crossovers would indicate the initiation of inspiration and expiration. However, fluctuations in the signal near the zero reference due to electrical and mechanical noise can produce false signals. In order to avoid false signals, inhalation and exhalation signals are compared to non zero reference limits. In order to maintain the sensitivity of the breath signal, the reference limits are varied as a function of the peaks of the patient air flow signal and of the derivative of the total air flow signal.

Figure 3:
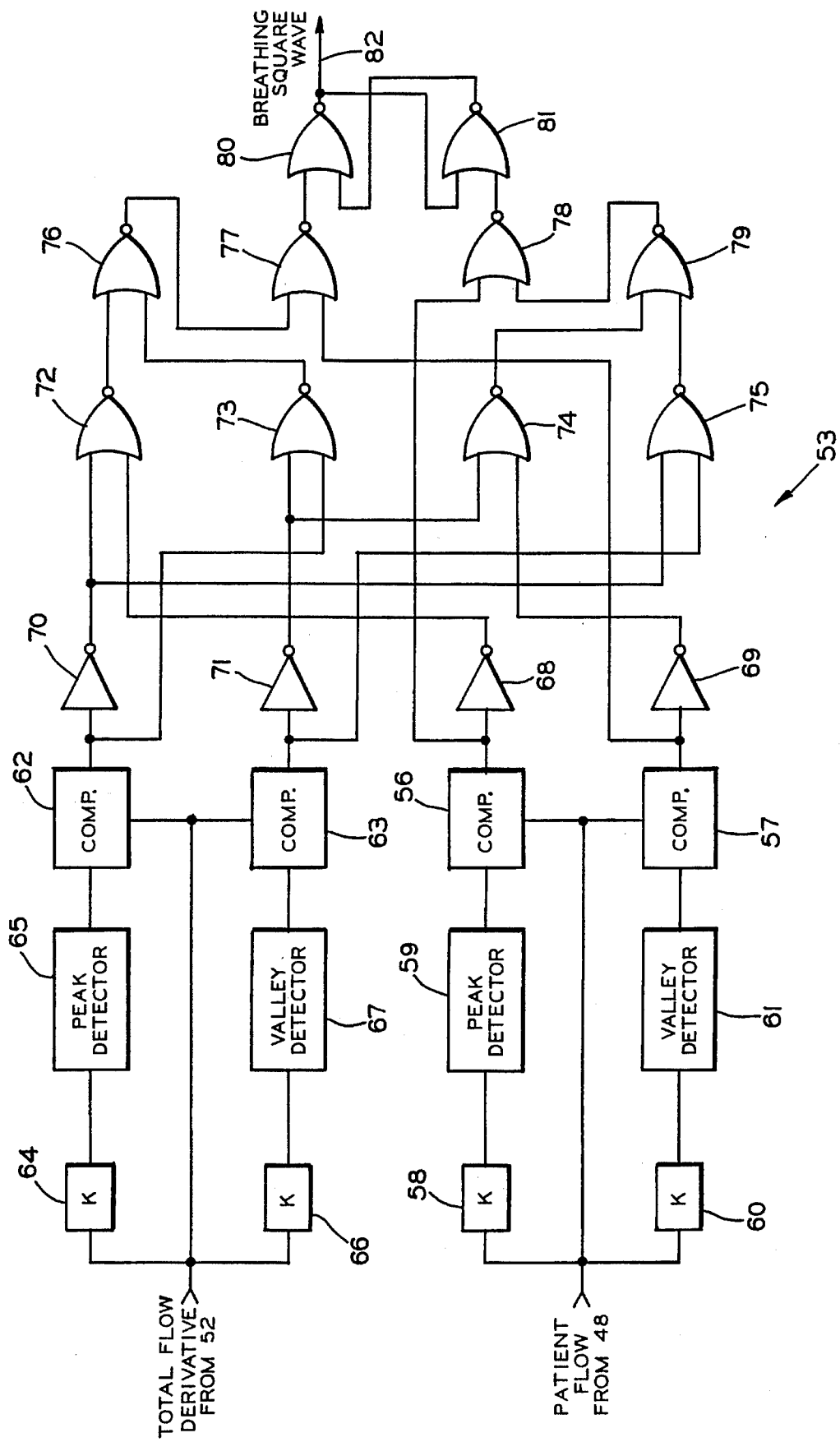
FIG. 3 is a schematic block diagram showing details of the logic for detecting the beginning of patient inspiration and expiration.

FIG. 3 is a schematic diagram of the logic 53 for creating a square wave breathing signal. The patient air flow signal from the high pass filter 48 (FIG. 2) is applied to on input of a peak comparator 56 and one input of a valley comparator 57 for comparison with a threshold level. The patient air flow signal also is passed through an amplifier 58, which reduces the signal level by a desired factor K to obtain the peak threshold limit on the signal peaks during inhalation, and onto a peak detector 59. The peak detector 59 produces a controlled slowly decaying output voltage having a maximum level of the peaks of the patient flow signal during inspiration. If the patient's breathing level decreases, the peak level will decrease to gradually decrease the threshold limit, while the threshold limit will immediately increase as the breathing level peaks increase. The comparator 56 generates an output whenever the level of the patient flow signal exceeds the level of the output from the peak detector 59 to indicate that inspiration is taking place. Similarly, the patient flow signal passes through an amplifier 60 to a valley detector 61 which produces a low level threshold limit voltage. The valley detector 61 is merely a peak detector which looks at the peaks of the inverse of the patient flow signal so that the signal level goes high during expiration. The comparator 57 compares the inverse of the patient flow signal with the output of the valley detector 61 and produces a high output level whenever the inverse of the patient flow signal is higher than the reference level signal from the valley detector 61 to indicate that expiration is taking place.

The total air flow derivative from the band pass filter 52 is processed in an identical manner to the patient air flow signal. The total air flow derivative is applied to one input to a peak comparator 62 and to one input to a valley comparator 63. The derivative signal also is applied through an amplifier 64 to a peak detector 65 and through an amplifier 66 to a valley detector 67. The comparator 62 generates a high output whenever the total flow derivative exceeds a reference level from the peak detector 65 and the comparator 63 generates a high output whenever the inverse of the total flow derivative exceeds a reference level from the valley detector 67.

The outputs from the four comparators 56, 57, 62 and 63 are applied, respectively, to the inputs of four inverters 68–71. The outputs from the comparators 56, 57, 62 and 63 and from the inverters 68–71 are combined by 8 NOR gates 72–79. The gate 72 has an input connected to the output from the inverter 68 and an input connected to the output of the inverter 70. The gate 73 has an input connected from the output of the comparator 62 and an input connected to the output of the inverter 71. The gate 74 has an input connected to the output of the inverter 69 and an input connected to the output of the inverter 71. The gate 75 has an input connected to the output of the inverter 70 and an input connected to the output of the comparator 63. The gate 76 has an input connected to the output of the gate 72 and an input connected to the output of the gate 73. The gate 77 has an input connected to the output of the gate 77 and an input connected to the output of the comparator 57. The gate 78 has an input connected to the output of the comparator 56 and an input connected to the output of the gate 79. Finally, the gate 79 has an input connected to the output of the gate 74 and an input connected to the output of the gate 75. A pair of NOR gates 80 and 81 are connected to form an RS latch. The output of the gate 81 is connected to one input to the gate 80 and the output of the gate 80 is connected to one input of the gate 81. An output 82 of the gate 77 is connected to the other input to the gate 80 and the output from the gate 78 is connected to the other input to the gate 81. The output 82 of the gate 80 is a square wave which goes high when inspiration begins and remains high until expiration begins, at which time it goes low. The signal will remain at a given level until there is a change between inspiration and expiration.

Inspiration is defined by the logic 53 as either the total flow derivative being above an upper limit and the patient flow signal being between upper and lower limits, or the patient flow signal being above an upper limit. Expiration is defined by the logic 53 as either the total flow derivative being below a lower limit and the patient flow signal being between upper and lower limits, or the patient flow signal being below a lower limit. This is accomplished by slowly discharging peak and valley detectors to adjust the switching limits to be appropriate to the instantaneous respiratory patterns. Small time delays may be added to the patient flow and total flow derivative switching signals in order to eliminate false triggering at low tidal volumes and breathing frequencies. If both the patient flow signal and the total flow derivative are within their respective limits, the breathing square wave remains at whatever value it achieved prior to the occurrence of this condition. Thus, once the square wave goes to a level indicating inspiration, it will remain at this level until expiration is detected and once expiration is detected, the square wave will go to and remain at the logic level indicating expiration until inspiration is again detected.

According to the present invention, the controller 17 operates the CPAP apparatus in any of three modes: a low pressure standby mode with the blower 12 operating at a low speed, a normal operating mode, and a standby mode with the blower 12 turned off. When the apparatus 10 is initially turned on, it enters the low pressure standby mode. While the apparatus is in either of the two standby modes, it monitors for breathing into the mask 11. If no mask breathing occurs within a predetermined time, such as 15 minutes, after the apparatus 10 enters the low pressure standby mode, the controller 17 turns the blower off to conserve energy, while continuing to monitor for mask breathing. When the patient begins breathing into the mask 11, the controller 17 senses the breathing and turns the blower 12 on if it was off and the controller 17 enters the normal operating mode. If the mask is removed from the patient or a gross leak occurs, for example, between the mask 11 and the patient's face, the controller 17 senses the unimpeded air flow and, after a short time, again places the blower 12 in one of the standby modes, such as the low pressure standby mode. After remaining in the low pressure standby mode for the predetermined time, the blower is switched off. Consequently, if a patient awakes during the night and temporarily removes the mask, the blower 12 reverts to the low pressure standby mode until the patient replaces and begins breathing into the mask. If the mask is not replaced within the predetermined time, the blower is stopped. If desired, an alarm may be sounded to alert the patient that the CPAP apparatus 10 has been placed in the standby mode, since the blower 12 also will automatically enter the standby mode if the mask is knocked off or removed while the patient continues to sleep. There have been observed instances of patients removing CPAP masks while sleeping.

As described above, the patient air flow signal and the total air flow signals may be used to produce a square wave signal which changes from a low level to a high level when the patient begins to inhale and changes from the high level to the low level when the patient begins to exhale. The leading edges or the signal level changes in the square wave breathing signal indicate the beginning of inhalation and the beginning of exhalation. The programmable microprocessor in the controller 17 can respond to the leading edges of the breathing signal to determine when breathing into the mask 11 has began for switching the blower from the standby mode to the normal operating mode. The microprocessor also can determine from the total flow signal and/or from the breathing signal when the mask has been removed and switch the blower back to the standby mode.

Figure 4:
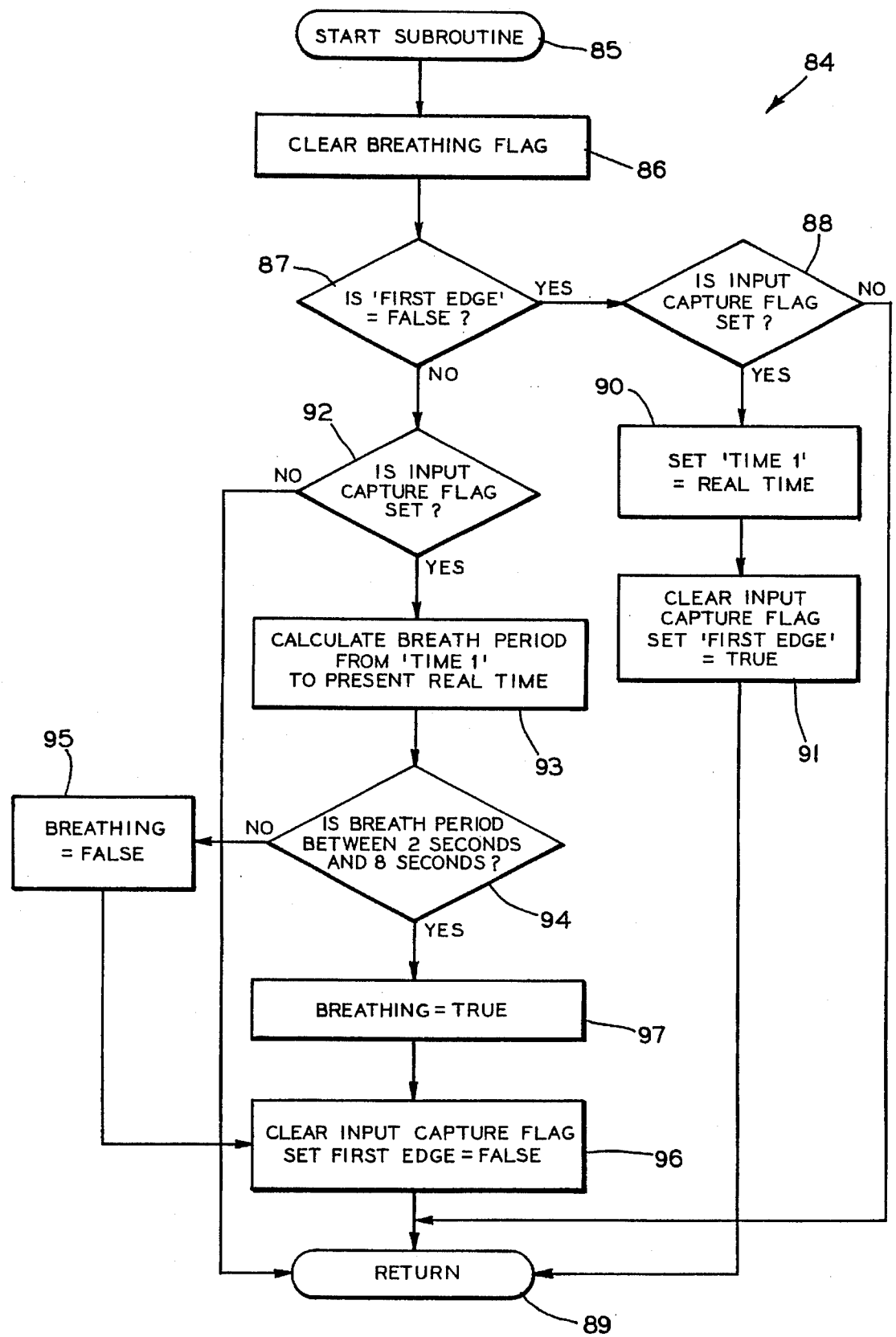
FIG. 4 is a logic flow diagram illustrating the automatic startup operation of the CPAP apparatus of FIG. 1 for switching from the standby mode to the normal operating mode.

FIG. 4 is a logic flow diagram illustrating a subroutine 84 for the microprocessor to determine when patient breathing into the mask 11 has began. An "input capture" flag is set each time the breathing square wave changes to a positive level at the beginning of an inspiration and remains set until cleared by the microprocessor. The subroutine 84 also uses a first edge flag and a breathing flag. The breathing flag is set true when breathing is detected and this flag tells the microprocessor to switch from the standby mode to the normal operating mode. The microprocessor cycles through the breathing subroutine on a periodic basis, for example, at a rate of 16 Hz., while the CPAP apparatus is in the standby mode.

The subroutine 84 is entered at a block 85 and passes through a block 86 wherein the breathing flag is cleared to a block 87. An inquiry is made at the block 87 as to whether the first edge flag is false. Prior to the first patient breath, the first edge flag is false and a block 88 asks if the capture flag is set. If the patient has not yet began breathing into the mask 11, the capture flag will not be set and the logic passes through a return block 89 to the main program in the microprocessor. This cycle will repeat at a rate of 16 times per second until the breathing square wave changes to a positive level indicating the beginning of inspiration. At that time, the input capture flag is set and during the next cycle through the subroutine 84 the block 88 causes a block 90 to store the present time as "time 1" in the microprocessor. The input capture flag then is cleared, the first edge flag is set to true and the subroutine passes through the return block 89 to the main program.

Since the first edge flag is now true, in the next cycle the control will pass from the block 87 to a block 92 which asks if the capture flag is set. The capture flag will not be reset until the patient begins a second breath into the mask. Until that time, the subroutine 84 passes from the block 92 to the return block 89. When the subroutine 84 is cycled immediately after the patient begins a second breath into the mask 11, the software passes from the block 92 to a block 93 which compares the stored time 1 with the present time to determine the breath period. A block 94 then looks at the breath period to determine if it falls within a normal breathing range. Normally, a person will breath at a rate of between 8 and 25 breaths per minute (BPM). For a preferred embodiment of the apparatus 10, it was decided to limit the breath period to between 2 seconds (30 BPM) and 8 seconds (7.5 BPM). If the breath period is outside of this range, the breathing flag is set to false at a block 95. Then the input capture flag is cleared and the first edge flag is set to false at a block 96 and the subroutine 84 is ended at the return block 89. On the other hand, if at the block 94 the breath period was found to be between 2 seconds and 8 seconds, the breathing flag is set at a block 97. The cycle then passes through the block 96 to clear the input capture flag and set the first edge flag false and onto the return block 89. Once the breathing flag is set to true, the microprocessor switches from the standby mode to the normal operating mode and no longer cycles through the subroutine 84.

Figure 5:
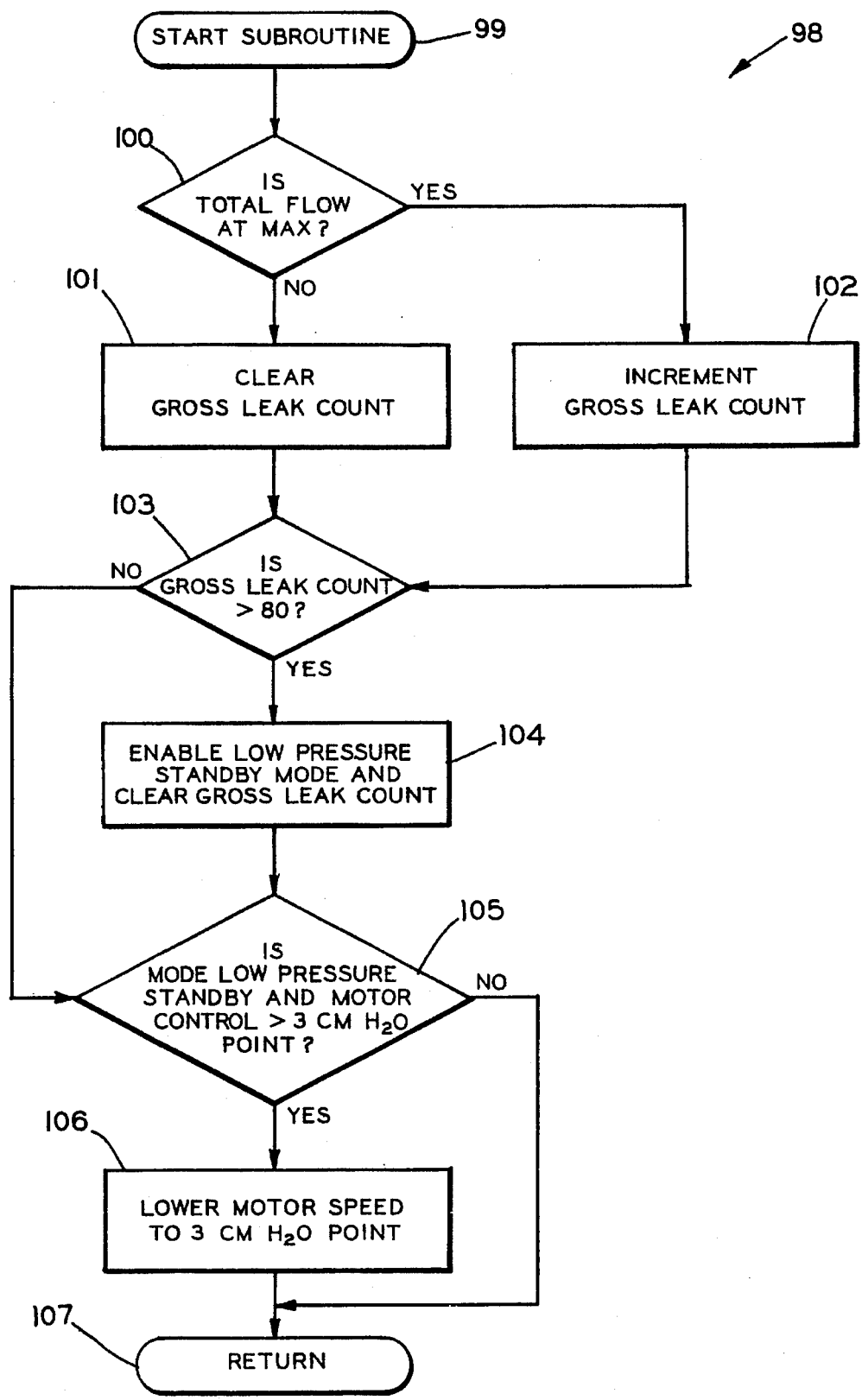
FIG. 5 is logic flow diagram illustrating the operation of the microprocessor for detecting gross air leaks in the CPAP apparatus of FIG. 1 for switching to the standby operating mode.

FIG. 5 is a logic flow diagram illustrating a subroutine 98 for causing the microprocessor to switch from a normal operating mode to a low pressure standby mode in the event of a gross air leak, for example, if the patient removes the mask 11 or if the mask 11 is moved to a position wherein the mask 11 fails to seal sufficiently against the patient's face. Each time the microprocessor cycles through its program at its 16 Hz. cycle time and the apparatus 10 is in the normal operating mode, the subroutine 98 is run. The subroutine 98 is entered at a block 99 and passes to a block 100 which asks if the total air flow is at a maximum, i.e., there is no air flow resistance at the mask. If the total flow is not at a maximum, a gross leak counter is cleared at a block 101 and, if the total flow is at a maximum, the gross leak counter is incremented by 1 at a block 102. In either event, a block 103 then compares the gross leak count with the number 80. At the 16 Hz. cycle rate, it will take a continuous maximum air flow for 5 seconds to increment the gross leak count to 80. If the air flow drops below the maximum at any time during the 5 seconds, the gross leak count is cleared. If the gross leak count exceeds 80, the low pressure standby mode is enables and the gross leak count is cleared at a block 104. During the standby mode, the blower pressure is set to equal or below 3 cm $H_2O$. If the gross leak count at the block 103 was not greater than 80 or if the low pressure standby mode was set at the block 104, a block 105 asks if the apparatus 10 is set to the low pressure standby mode and also if the blower motor is operated to produce a pressure greater than the 3 cm $H_2O$ point. If both questions are affirmative, the blower motor speed is reduced at a block 106 to the 3 cm $H_2O$ pressure point and the subroutine returns at a block 107 to the main program. If either the apparatus 10 is not in the low pressure standby mode or the pressure is not greater than 3 cm $H_2O$ at the block 105, the subroutine goes directly to the return block 107 without changing the blower motor speed. The apparatus 10 will remain in the low pressure standby mode either until mask breathing is detected and the normal operating mode is restarted or until the elapse of a predetermined time, such as 15 minutes, and the blower off standby mode is entered.

Since the blower is operated in the normal mode only while a patient breaths into the mask and there are no gross mask leaks, the blower operating time is an accurate indication of the time that the patient uses the apparatus 10. This information is often useful to the patient's physician or respiratory therapist.

It will be appreciated that the scope of the claimed invention is broader than the above described preferred embodiment of the invention. For example, a specific method and apparatus were described for generating a signal indicative of patient breathing. Other known methods for generating a breathing signal are equally applicable to the invention. Pressure changes in the mask are sometimes used to generate a breathing signal. Or, chest contractions and expansions can be used to generate a breathing signal, although this is not as accurate as the method used in the preferred embodiment. Further, it will be appreciated that the control function may be achieved either digitally with a programmable microprocessor or through an analog electric circuit. Various other modifications and changes may be made to the above described preferred embodiment of CPAP apparatus without departing from the spirit and the scope of the following claims.

We claim:

1. A method for controlling CPAP apparatus which applies a positive airway pressure to a patient, said apparatus including an air blower and means for applying a positive air pressure from said blower to a mask adapted to be secured to a patient in communications with the patient's respiratory airway, said method comprising the steps of:

a) placing said CPAP apparatus in a standby mode;

b) sensing the initiation of patient breathing through said mask; and c) automatically switching said CPAP apparatus from said standby mode to an operating mode in response to the sensing of a patient breathing through said mask to apply a continuous positive airway pressure to such patient.

2. A method for controlling CPAP apparatus, as set forth in claim 1, wherein when CPAP apparatus is switched to an operating mode in response to the sensing of patient breathing through said mask, said CPAP apparatus initially applying a predetermined low positive airway pressure to such patient for a predetermined time and subsequently increasing the applied positive airway pressure to a prescribed level.

3. A method for controlling CPAP apparatus, as set forth in claim 1, and further including the steps of sensing when said mask in no longer in communications with the patient's airway and returning said CPAP apparatus to the standby mode in response to the sensing of said mask no longer being in communication with the patient's airway.

4. A method for controlling CPAP apparatus, as set forth in claim 3, wherein the mask is sensed as no longer being in communication with the patient's airway by sensing when the air flow to said mask is substantially unrestricted.

5. A method for controlling CPAP apparatus, as set forth in claim 3, wherein when CPAP apparatus is switched to an operating mode in response to the sensing of patient breathing through said mask, said CPAP apparatus initially applying a predetermined low positive airway pressure to such patient for a predetermined time and subsequently increasing the applied positive airway pressure to a prescribed level.

6. A method for controlling CPAP apparatus, as set forth in claim 3, and further including the step of measuring the total time that a patient breathes through said mask.

7. A method for controlling CPAP apparatus, as set forth in claim 6, wherein the total time that a patient breathes through said mask is measured by measuring the total time said apparatus is in said operating mode.

8. A method for controlling CPAP apparatus, as set forth in claim 1, and further including the step of generating an inhalation pulse signal each time the patient inhales into said mask, and wherein initiation of patient breathing through said mask is sensed by detecting a predetermined number of inhalation pulses in a predetermined time interval.

9. A method for controlling CPAP apparatus, as set forth in claim 8, and further including the step of generating an exhalation pulse signal each time the patient exhales into said mask, and wherein initiation of patient breathing through said mask is sensed by detecting a predetermined number of inhalation and exhalation pulses in a predetermined time interval.

10. A method for controlling CPAP apparatus, as set forth in claim 1, wherein while said apparatus is initially in said standby mode placing said blower in a low pressure standby mode, and stopping said blower after said blower remains a predetermined time in said low pressure standby mode.

11. A method for controlling CPAP apparatus, as set forth in claim 10, wherein the initiation of patient breathing through said mask includes the steps of both sensing when a patient is breathing through said mask while said blower is in said low pressure standby mode and sensing when a patient is breathing through said mask while said blower in a stopped blower standby mode.

12. In a method for controlling CPAP apparatus which includes the step of applying a positive airway pressure to a patient from an air blower connected to a mask adapted to be secured to a patient in sealed communications with the patient's respiratory airway, the improvement comprising the steps of sensing gross air leaks resulting from said mask no longer being in sealed communication with the patient's airway, and placing said apparatus in a reduced pressure standby mode in response to sensing such gross air leaks.

13. A method for controlling CPAP apparatus, as set forth in claim 12, wherein gross air leaks are sensed by sensing when air flow to said mask is substantially unrestricted.

14. A method for controlling CPAP apparatus, as set forth in claim 12, and including the step of placing said blower in a low pressure standby mode when said apparatus is initially placed in a standby mode.

15. A method for controlling CPAP apparatus, as set forth in claim 14, and further including the step of stopping said blower after said blower remains a predetermined time in said low pressure standby mode.

16. In apparatus for applying a continuous positive airway pressure to a patient's respiratory system including a blower for establishing a positive air pressure, a mask adapted for sealed communication with a patient's nose, and a hose supplying pressurized air from said blower to said mask, an improved control comprising means for operating said blower in a standby mode and in a normal mode, means for detecting when a patient begins breathing into said mask, and means responsive to the detection of patient breathing into said mask for changing the operation of said blower from said standby mode to said normal mode.

17. A control for apparatus for applying a continuous positive airway pressure to a patient's respiratory system, as set forth in claim 16, and further including means for detecting an unrestricted flow of air through said mask, and means for returning said blower to said standby mode in response to the detection of such unrestricted air flow from said mask.

18. A control for apparatus for applying a continuous positive airway pressure to a patient's respiratory system, as set forth in claim 17, and further including means for measuring the time said blower is operated in the normal mode.

19. A control for apparatus for applying a continuous positive airway pressure to a patient's respiratory system, as set forth in claim 17, and further including means for operating said blower at a predetermined low speed in a first standby mode and means for stopping said blower in a second standby mode, wherein said means for returning said blower to said standby mode returns said blower to said first standby mode, and further including means responsive to said blower remaining in said first standby mode for a predetermined time for switching said blower to said second standby mode.

* * * * *